Jan. 16, 1934. W. UECKER Plant Pat. 85
APPLE TREE
Filed May 9, 1932
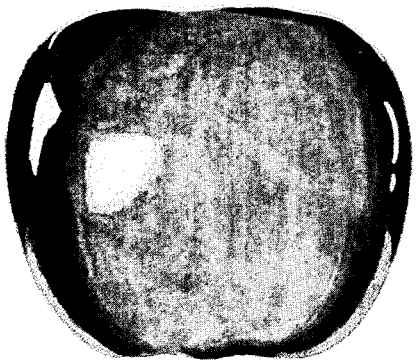
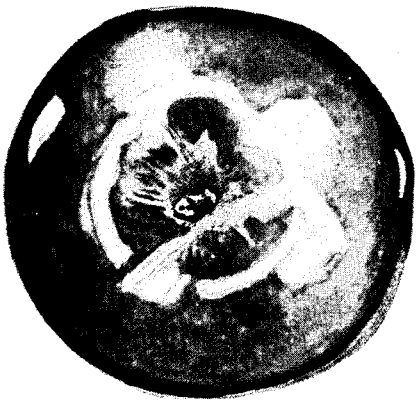
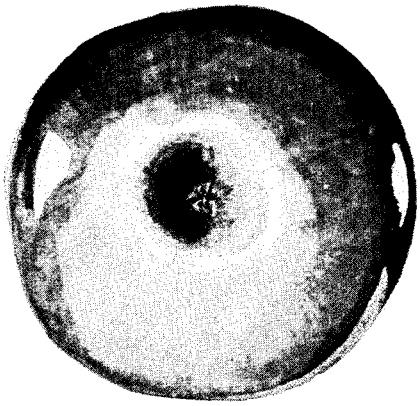
Inventor:
William Uecker
By Robb & Robb
Attorneys Patented Jan. 16, 1934

Plant Pat. 85

UNITED STATES PATENT OFFICE

85

APPLE TREE

William Uecker, Cashmere, Wash., assignor to Stark Bro's Nurseries & Orchards Company, Louisiana, Mo.

Application May 9, 1932. Serial No. 610,183

1 Claim. (Cl. 47—62)

This discovery relates to a new variety of apple tree, the most notable and distinctive features of which reside in the earlier coloring and the deep blazing all-over red color of its fruit as compared with those varieties which most nearly resemble the same when grown under comparable conditions.

From a commercial standpoint, this is a most valuable and long desired characteristic in that it enables the apple grower to obtain first-on-the market prices and at the same time the coloring is sufficiently developed to come within the extra fancy grade which commands the higher prices and consequent higher profits. Generally, the best profits on an apple crop of the Jonathan type apple are made on the first shipments because of the higher prices usually obtained, whereas after the large later shipments reach the market and the market becomes well supplied or glutted so to speak, the prices drop and the later shipments often result in an actual loss to the grower. Frequently, apples are left on the tree until they are overripe in order to obtain color, that is, such color as to come within the higher priced grades. It is quite well known that there is a much greater commercial demand for highly colored apples, preferably red, because of their attractiveness or appeal to the public eye and because of the longer keeping quality. Early coloring of the fruit enables the grower to pick the fruit when it is hard ripe, thereby still further increasing the keeping quality. Also, red apples do not scald as readily. From this it will be seen that a deep blazing all-over red colored apple is very valuable, particularly insofar as marketability, commercial demand, and price or profit is concerned.

The Jonathan variety of apple, from which the new variety originated as a sport, bears a closer resemblance to the new variety than any other variety. In fact the characteristics of these varieties are substantially the same in all respects except in time of coloring and color of the fruit. The fruit of the new variety attains its color approximately two weeks earlier than the Jonathan fruit, the usual color of the latter being lighter and more or less striped or splashed as distinguished from the deep blazing all-over or solid red color of the new variety.

From the foregoing the predominant characteristics of the new variety will be apparent, but a more detailed technical description of the fruit is given as follows, bearing in mind that the distinctiveness of the new variety resides primarily in the fruit and not in the tree which latter is substantially the same as and typically Jonathan:

*Fruit*

*Size.*—Medium, resembling the Jonathan fruit in this respect.

*Form.*—Round conic to round ovate, also typically Jonathan.

*Stem.*—Medium, cavity acute, deep and symmetrical although very lightly furrowed.

*Calyx.*—Small, closed.

*Basin.*—Rather deep, abrupt, and prominently furrowed—not quite as regular as the usual midwestern grown Jonathan.

*Skin.*—Thick, tough and smooth, bright greenish yellow entirely overspread with a lively but deep glossy red. When well colored, the fruit is substantially entirely covered with this solid red, markedly contrasting with the Jonathan fruit which has a striped and mottled appearance and much less color when picked at the same time and when grown under comparable conditions. The dots on the skin of the new variety are very small and inconspicuous.

*Calyx tube.*—Rather small, short, funnel form.

*Stamens.*—Basal.

*Core.*—Medium in size, cell symmetrical.

*Seeds.*—Medium long, acute, numerous.

*Flesh.*—Whitish with yellow tinge, firm, rather fine, crisp, tender, juicy, and quite aromatic. The flesh and quality are typical of the Jonathan variety.

Having set forth the most notable features of the invention by comparison with that variety which most nearly resembles the same it is apparent that the new apple tree, which has been asexually reproduced, is clearly endowed with individual identity and is characterized truly as a new and distinct variety, as manifested particularly by the early coloring characteristic and deep blazing all-over red color of its fruit.

What I claim as new is:—

A new and distinct variety of apple tree characterized particularly by the early coloring of its fruit, as described, said fruit having a deep blazing all-over red color, as shown.

WILLIAM UECKER.